United States Patent
Andreoni et al.

(10) Patent No.: US 8,622,975 B2
(45) Date of Patent: Jan. 7, 2014

(54) MAGNETIC SAFETY NEEDLE ASSEMBLY

(75) Inventors: Todd Andreoni, Lyndhurst, NJ (US);
Gerry Bogert, Maywood, NJ (US);
Joshua Horvath, Sparta, NJ (US)

(73) Assignee: Becton, Dickinson & Company,
Franklin Lakes, NJ (US)

( * ) Notice: Subject to any disclaimer, the term of this patent is extended or adjusted under 35 U.S.C. 154(b) by 448 days.

(21) Appl. No.: 12/814,085

(22) Filed: Jun. 11, 2010

(65) Prior Publication Data
US 2011/0306937 A1    Dec. 15, 2011

(51) Int. Cl.
*A61M 5/32*    (2006.01)

(52) U.S. Cl.
USPC .......................................... 604/198; 604/192

(58) Field of Classification Search
USPC ............ 604/110, 111, 164.08, 171, 187, 192, 604/197–199; 206/363–368
See application file for complete search history.

(56) References Cited

U.S. PATENT DOCUMENTS

| | | | |
|---|---|---|---|
| 3,134,380 A * | 5/1964 | Armao | 604/198 |
| 4,702,739 A * | 10/1987 | Milorad | 604/198 |
| 5,163,917 A * | 11/1992 | Huefner et al. | 604/198 |
| 6,113,620 A | 9/2000 | Chung | |
| 7,238,169 B2 * | 7/2007 | Takagi et al. | 604/110 |
| 7,413,562 B2 * | 8/2008 | Ferguson et al. | 604/263 |
| 2006/0161108 A1 * | 7/2006 | Mogensen et al. | 604/164.01 |
| 2008/0086089 A1 * | 4/2008 | Isaacson et al. | 604/164.08 |
| 2009/0071502 A1 * | 3/2009 | Drugeon | 132/293 |
| 2011/0152832 A1 * | 6/2011 | Foshee et al. | 604/506 |

* cited by examiner

*Primary Examiner* — Kami A Bosworth

(74) *Attorney, Agent, or Firm* — Hoffmann & Baron, LLP

(57) ABSTRACT

A safety needle assembly is provided herein which includes a hub; a needle fixed to the hub, the needle having a distal end formed for insertion into a patient; a shield moveable relative to the hub from a first position, where the shield covers the distal end of the needle, to a second position, where the distal end of the needle is exposed and not covered by the shield; a first magnetic element fixed to the hub; and, a second magnetic element fixed to the shield. The first and second magnetic elements are configured so as to define a repulsive force therebetween which urges the first and second magnetic elements apart. The repulsive force urges the shield towards the first position. Advantageously, with the subject invention, a safety needle assembly may be provided which includes a minimal number of parts, without sacrificing reliability.

3 Claims, 4 Drawing Sheets

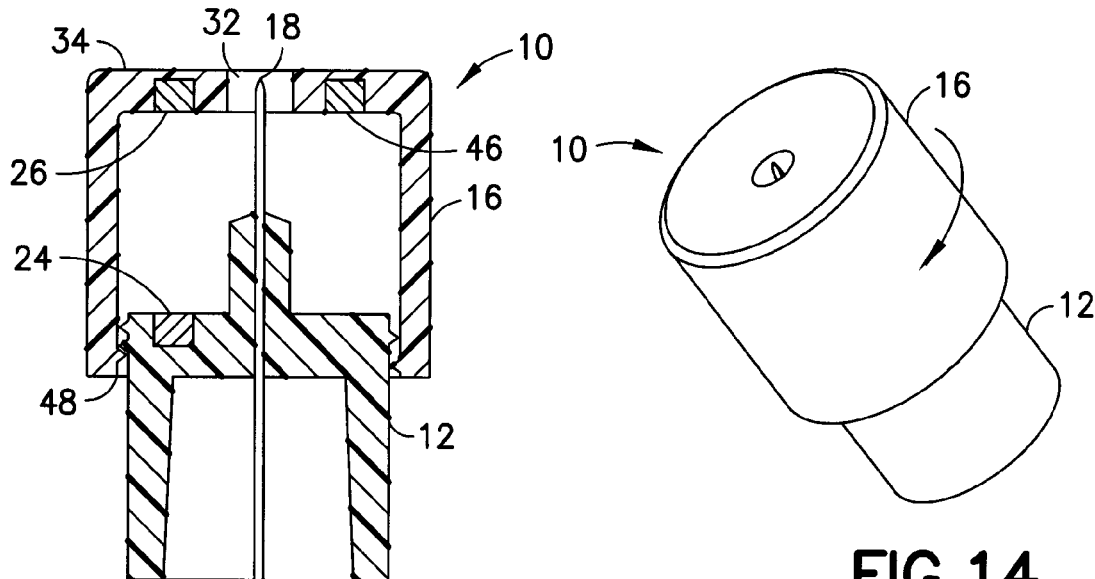
FIG. 13
FIG. 14
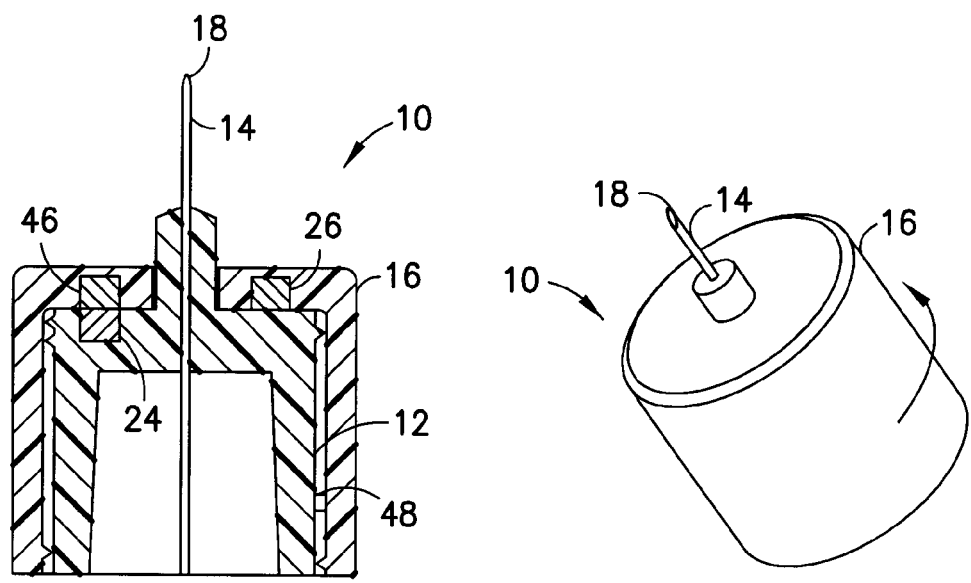
FIG. 15
FIG. 16

MAGNETIC SAFETY NEEDLE ASSEMBLY

FIELD OF THE INVENTION

This invention relates to needle assemblies for injectors and, more particularly, to safety needle assemblies.

BACKGROUND OF THE INVENTION

Safety needle assemblies are known in the prior art including safety pen needle assemblies for use with pen injectors. The assemblies are typically individually mountable to an injector. After injection, the assemblies are configured to shield the used needle to prevent a user from inadvertently receiving a "needle stick". Typically, the assembly is formed to be removable from the injector and disposed after use.

Costs considerations and high reliability are significant factors for safety needle assemblies. As such, a minimal number of parts is generally desired.

SUMMARY OF THE INVENTION

A safety needle assembly is provided herein which includes: a hub; a needle fixed to the hub, the needle having a distal end formed for insertion into a patient; a shield moveable relative to the hub from a first position, where the shield covers the distal end of the needle, to a second position, where the distal end of the needle is exposed and not covered by the shield; a first magnetic element fixed to the hub; and, a second magnetic element fixed to the shield. The first and second magnetic elements are configured so as to define a repulsive force therebetween which urges the first and second magnetic elements apart. The repulsive force urges the shield towards the first position. Advantageously, with the subject invention, a safety needle assembly may be provided which includes a minimal number of parts, without sacrificing reliability.

These and other features of the invention will be better understood through a study of the following detailed description and accompanying drawings.

BRIEF DESCRIPTION OF THE DRAWINGS

FIGS. 9-16 show variations of a safety needle assembly including at least three magnetic elements.

DETAILED DESCRIPTION OF THE INVENTION

Figure 1:
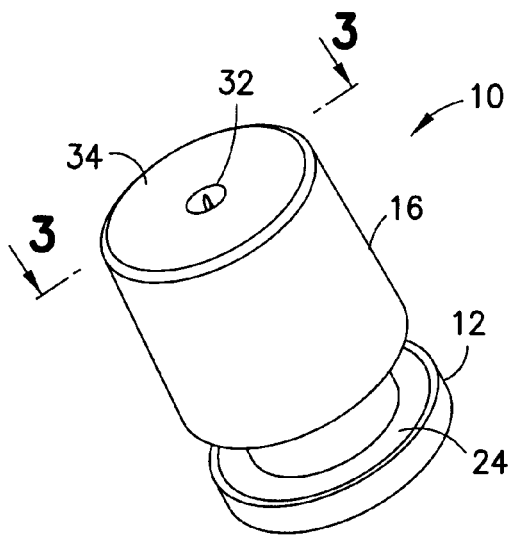
FIGS. 1 and 2 show, respectively, a safety needle assembly formed in accordance with the subject invention in shielding and non-shielding positions.

With reference to the Figures, a safety needle assembly 10 is shown which generally includes a hub 12, to which is fixed a needle 14, and a shield 16. The needle 14 may be of any known type and includes a distal end 18, formed for insertion into a patient, a proximal end 20, and a lumen 22 extending therebetween.

As used herein, the term "distal", and derivatives thereof, refers to a direction towards a patient during use, while, the term "proximal", and derivatives thereof, refers to a direction away from a patient during use.

Figure 2:
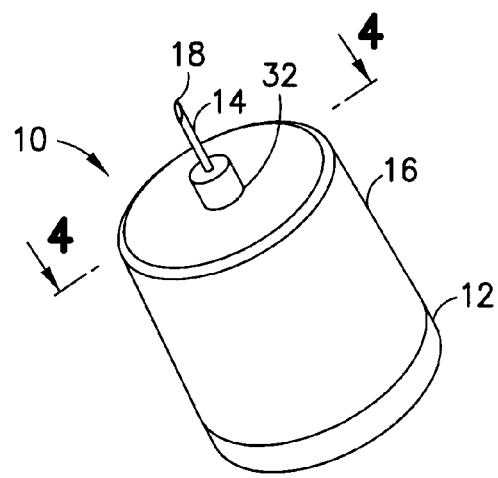

With reference to FIGS. 1 and 2, the shield 16 is moveable relative to the hub 12, particularly from a first position, shown in FIG. 1, where the shield 16 covers the distal end 18 of the needle 14, to a second position, shown in FIG. 2, where the distal end 18 of the needle 14 is exposed and not covered by the shield 16. In the second position, the needle 14 is available for use.

In a first embodiment of the subject invention, it is preferred that the shield 16 be maintained in the first position as shown in FIG. 1. To this end, a first magnetic element 24 is fixed to the hub 12 and a second magnetic element 26 is fixed to the shield 16. The first and second magnetic elements 24, 26 are configured so as to define a repulsive force therebetween which urges the first and second magnetic elements 24, 26 apart. For example, the magnetic poles of the first and second magnetic elements 24, 26 may be arranged to coact so as to generate the repulsive force. The repulsive force urges the shield 16 towards the first, shielding position.

Figure 3:
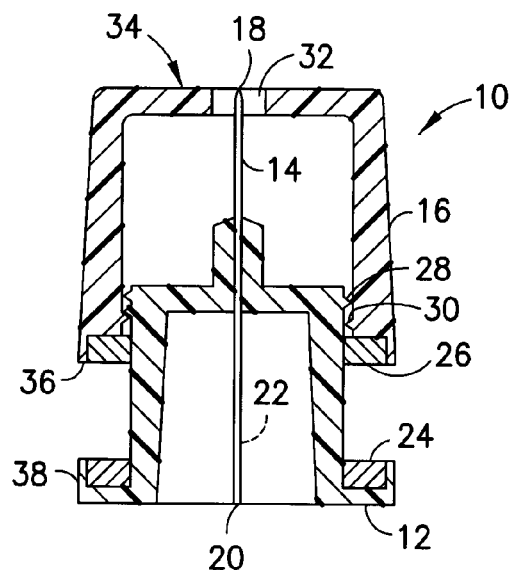
FIG. 3 is a cross-sectional view taken along line 3-3 of FIG. 1.
Figure 4:
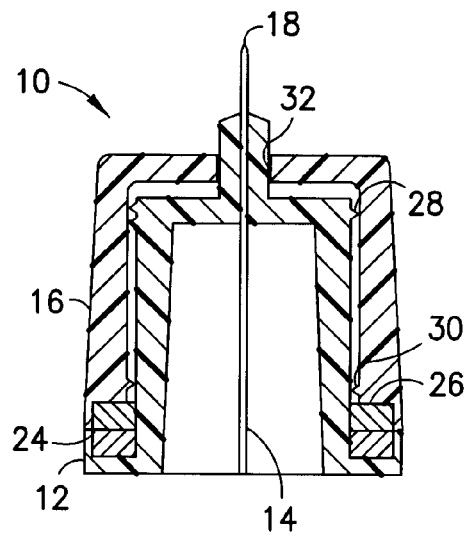
FIG. 4 is a cross-sectional view taken along line 4-4 of FIG. 2.

Preferably, features are defined on the hub 12 and/or the shield 16 which limit the extent of distal movement of the shield 16 relative to the hub 12. In this manner, excessive distal movement of the shield 16, which may lead to separation of the shield 16 from the hub 12, may be avoided. By way of non-limiting example, as shown in FIG. 3, the features may include at least one first detent 28 formed on the hub 12 and at least one second detent 30 formed on the shield 16. The first and second detents 28, 30 may be configured to interferingly engage and limit the extent of distal movement of the shield 16 relative to the hub 12. The first and second detents 28, 30 are configured to limit movement of the shield 16 to a position coinciding with the first, shielding position. It is noted that aperture 32 is defined in the shield 16 through which the needle 14 passes with the shield 16 moving from the first to the second positions. The distal end 18 of the needle 14 may be located in the aperture 32 in the first, shielding position, as shown in FIG. 3. The distal end 18 of the needle 14 may be shielded with the distal end 18 of the needle 14 being located in the aperture 32, yet proximally of distalmost end 34 of the shield 16.

To facilitate manufacturing, the first and second detents 28, 30 may be formed as cooperating threads which permit threading of the shield 16 onto the hub 12 with the second detent 30 ultimately completely by-passing the first detent 28. As will be appreciated by those skilled in the art, various configurations of the first and second detents 28, 30 may be utilized in connection with the subject invention.

Preferably, the first and second magnetic elements 24, 26 are axially aligned to maintain proper magnetic polar alignment. More preferably, the first and second magnetic elements 24, 26 are annularly formed to minimize any effect due to rotational displacement of the hub 12 and/or the shield 16. The first and second magnetic elements 24, 26 may be located on the respective peripheries of the hub 12 and the shield 16, as shown in FIGS. 1-4. More particularly, the second magnetic element 26 may be fixed to a proximal end 36 of the shield 16 with the first magnetic element 24 being fixed to an outwardly protruding flange 38. Alternatively, as shown in the embodiment of FIGS. 5-8, the first and second magnetic elements 24, 26 may be fixed to internal faces of the hub 12 and the shield 16. More particularly, the first magnetic element 24 may be fixed to distal face 40 of the hub 12. The distal face 40 circumscribes the needle 14. The second magnetic element 26 may be fixed to proximal face 42 which circumscribes the aperture 32. In both configurations, the first and second magnetic elements 24, 26 are preferably axially aligned.

The first and second magnetic elements 24, 26 may be fixed to the hub 12 and to the shield 16 in any known manner. For example, the first and second magnetic elements 24, 26 may be molded, e.g., overmolded, to the hub 12 and the shield 16, respectively. Fusion, e.g., ultrasonic or laser welding, or adhesion may be also utilized. Further, mechanical connection, such as by press fit or interference fit, may be also utilized.

Figure 5:
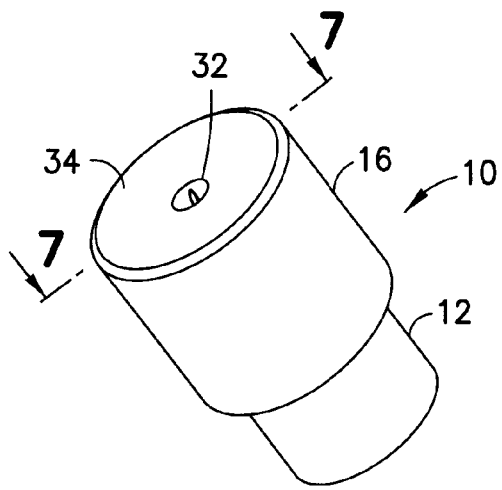
FIGS. 5 and 6 show, respectively, a variation of a safety needle assembly in shielding and non-shielding positions.

With the safety needle assembly 10 shown in FIGS. 1-8, the needle 14 is initially covered with the shield 16 being in the first, shielding position, as shown in FIGS. 1 and 5. In this manner, the needle 14 is completely covered prior to use. The hub 12 may be provided with needle mounting features 44 (FIG. 7), such as threads and/or a surface configuration (e.g., a Luer surface), configured for mounting the safety needle assembly 10 onto a medical injector. With the needle mounting features 44, the safety needle assembly 10 may be formed to be removable after use. Alternatively, the safety needle assembly 10 may be rigidly fixed to a medical injector, such as by adhesion or fusion, or formed integral with the barrel or other component of a medical injector. Preferably, with the needle mounting features 44 being provided, the hub 12 is engaged to cause mounting of the safety needle assembly 10.

Figure 6:
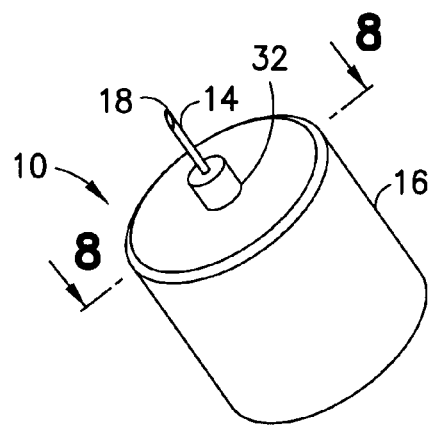
Figure 7:
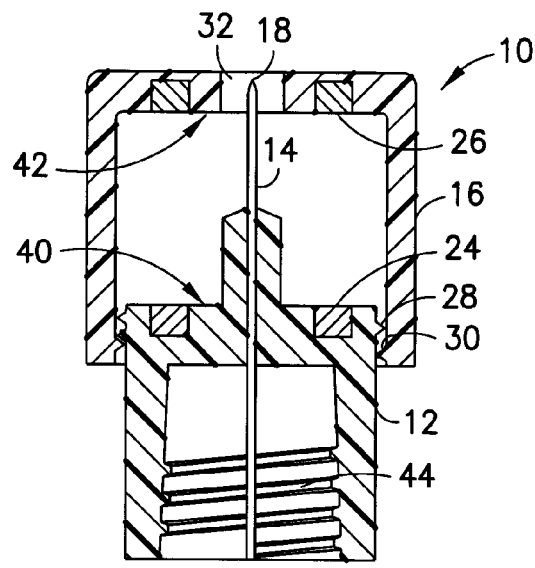
FIG. 7 is a cross-sectional view taken along line 7-7 of FIG. 5.
Figure 8:
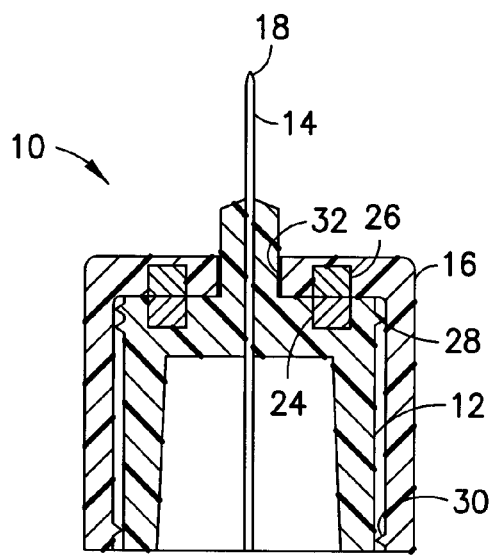
FIG. 8 is a cross-sectional view taken along line 8-8 of FIG. 6.

With the safety needle assembly 10 being prepared and ready for injection, the shield 16 is applied to a patient's skin with pressure being applied to the hub 12 through the corresponding injector. As shown in FIGS. 2 and 6, with a predetermined level of force, the repulsive force generated between the first and second magnetic elements 24, 26 is overcome and the hub 12 is moved distally relative to the shield 16. With the hub 12 moving distally relative to the shield 16, the needle 14 becomes exposed, as shown in FIGS. 2 and 6. This exposure also allows insertion of the needle 14 into a patient. The repulsive force generated by the first and second magnetic elements 24, 26 is surmountable by a predetermined amount of force applied to the hub 12 relative to the shield 16. Once injection is complete, and the pressing force is removed from the hub 12, the shield 16 is urged distally relative to the hub 12 under force of movement of the repulsive force generated by the first and second magnetic elements 24, 26 to return to the first, shielding position.

Figure 9:
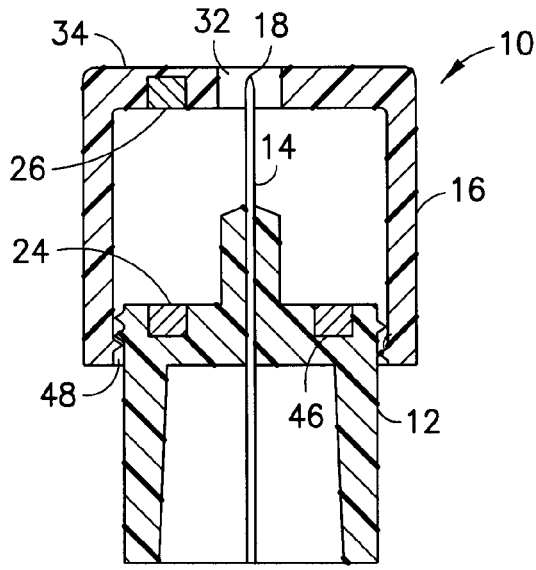
Figure 10:
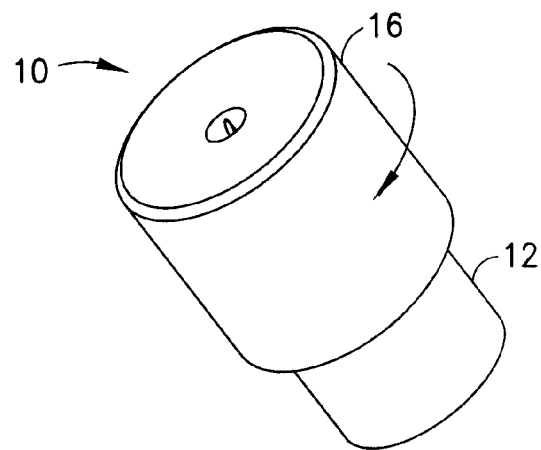
Figure 11:
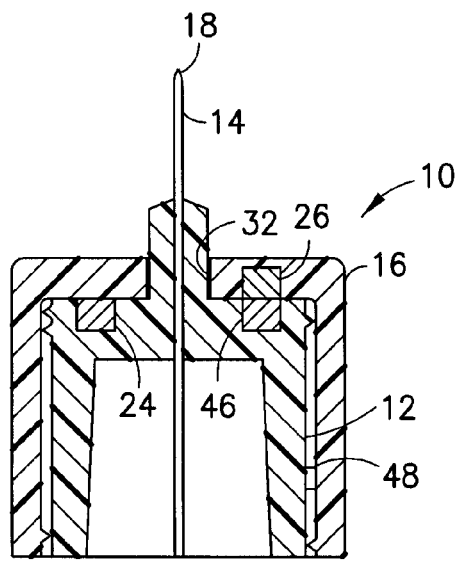
Figure 12:
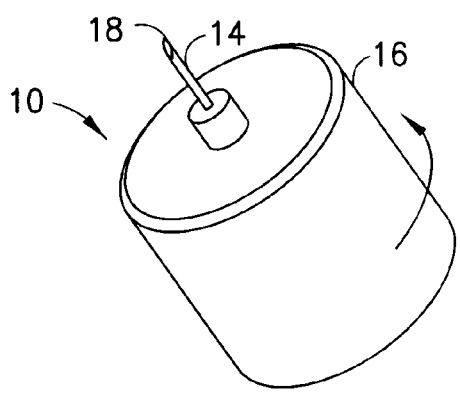

With reference to FIGS. 9-16, a third magnetic element 46 may be provided on the hub 12 or the shield 16 to provide different modes of operation of the safety needle assembly 10. It is preferred that the third magnetic element 46 be located on the hub 12 or the shield 16 at a location diametrically opposite the first or second magnetic element 24, 26. In addition, the third magnetic element 46 is configured to provide an opposite magnetic pole from the corresponding magnetic element located on the hub 12 or the shield 16 with the third magnetic element 46. Thus, with reference to FIGS. 9-12, the third magnetic element 46 may be fixed to the hub 12 with the first magnetic element 24 with the first and third magnetic elements 24, 46 having opposite magnetic poles facing the shield 16. In this manner, rotational alignment of the second magnetic element 26 with the first or third magnetic element 24, 46 will result in magnetic attraction or repulsion, depending on the polarity of the aligned magnetic elements. Thus, where initial exposure of the needle 14 is desired, the shield 16 may be rotationally aligned so as to generate a magnetic attractive force between the second and third magnetic elements 26, 46, resulting in the shield 16 being drawn to the hub 12. In this manner, as shown in FIGS. 11 and 12, the shield 16 is in the second position with the needle 14 being exposed for use. The shield 16 may be rotationally adjusted relative to the hub 12 so that the second magnetic element 26 aligns with the first magnetic element 24, as shown in FIGS. 9 and 10, resulting in a magnetically repulsive force being generated therebetween and the shield 16 being urged away from the hub 12 to the first, shielding position. To limit inadvertent rotation of the shield 16 relative to the hub 12, one or more releasable retaining arrangements 48 may be provided between the shield 16 and the hub 12, such as a releasable tongue and groove arrangement. The releasable retaining arrangements 48 may be positioned to provide releasable retention with the magnetic elements aligned as shown in FIGS. 9 and 11, respectively.

As will be appreciated by one skilled in the art, the third magnetic element 46 may be mounted onto the shield 16 with the second magnetic element 26, as shown in FIGS. 13-16. Here, the third magnetic element 46 is formed to have the opposite magnetic polarity from the second magnetic element 26 facing the hub 12. Rotational adjustment of the shield 16 relative to the hub 12 shall result in movement of the shield 16 between the first position (FIGS. 13 and 14) and the second position (FIGS. 15 and 16), in the same manner as described above.

Various quantities and configurations of the magnetic elements may be utilized. Preferably, the first-third magnetic elements 24, 26, 46 are not annular shaped in the embodiments of FIGS. 9-16. In all other respects, considerations discussed above with respect to FIGS. 1-8 apply equally to the embodiments of FIGS. 9-16.

What is claimed is:

1. A safety needle assembly comprising:
a hub;
a needle fixed to said hub, said needle having a distal end formed for insertion into a patient;
a shield movable relative to said hub from a first position, where said shield covers said distal end of said needle, to a second position, where said distal end of said needle is exposed and not covered by said shield;
a first annular magnetic element fixed to said hub about said needle; and,
a second annular magnetic element fixed to said shield;
wherein, said first and second magnetic elements are aligned and configured so as to define a repulsive force therebetween which urges said first and second magnetic elements apart, said repulsive force urging said shield toward said first position, and,
wherein, said repulsive force being surmountable by a predetermined level of force which causes said shield to move relative to said hub from said first position to said second position.

2. A safety needle assembly comprising:
a hub;
a needle fixed to said hub, said needle having a distal end formed for insertion into a patient;
a shield movable relative to said hub from a first position, where said shield covers said distal end of said needle, to a second position, where said distal end of said needle is exposed and not covered by said shield, said shield having proximal and distal ends, said proximal end not being rotationally fixed to said hub;
a first magnetic element fixed to said hub;
a second magnetic element fixed to said shield; and,
a third magnetic element fixed to said hub;
wherein, said first and second magnetic elements are configured so as to define a repulsive force therebetween which urges said first and second magnetic elements apart, said repulsive force urging said shield toward said first position, wherein, said second and third magnetic elements being configured so as to define an attractive force therebetween which urges said second and third magnetic elements together, said attractive force urging said shield to said second position, and, wherein said shield is rotationally adjustable relative to said hub so as to selectively align said second magnetic element with said first and third magnetic elements.

3. A safety needle assembly comprising:

a hub;

a needle fixed to said hub, said needle having a distal end formed for insertion into a patient;

a shield movable relative to said hub from a first position, where said shield covers said distal end of said needle, to a second position, where said distal end of said needle is exposed and not covered by said shield, said shield having proximal and distal ends, said proximal end not being rotationally fixed to said hub;

a first magnetic element fixed to said hub;

a second magnetic element fixed to said shield; and, a third magnetic element fixed to said shield;

wherein, said first and second magnetic elements are configured so as to define a repulsive force therebetween which urges said first and second magnetic elements apart, said repulsive force urging said shield toward said first position, wherein, said first and third magnetic elements being configured so as to define an attractive force therebetween which urges said first and third magnetic elements together, said attractive force urging said shield to said second position, and, wherein said shield is rotationally adjustable relative to said hub so as to selectively align said first magnetic element with said second and third magnetic elements.

\* \* \* \* \*